(12) United States Patent  
Monda et al.

(10) Patent No.: US 7,753,965 B2
(45) Date of Patent: Jul. 13, 2010

(54) HAIR DYE COMPOSITION

(75) Inventors: Keiji Monda, Sumida-ku (JP); Silvio Aime, Turin (IT); Carlo Nervi, Turin (IT); Simona Baroni, Turin (IT); Simona Ghiani, Turin (IT); Giovanni Battista Giovenzana, Novara (IT)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/375,677

(22) PCT Filed: Jul. 31, 2007

(86) PCT No.: PCT/JP2007/000817

§ 371 (c)(1),
(2), (4) Date: Jan. 30, 2009

(87) PCT Pub. No.: WO2008/015785

PCT Pub. Date: Feb. 7, 2008

(65) Prior Publication Data

US 2010/0000564 A1 Jan. 7, 2010

(30) Foreign Application Priority Data

Jul. 31, 2006 (JP) .............................. 2006-207546

(51) Int. Cl.
*A61Q 5/10* (2006.01)
*C07D 243/00* (2006.01)
(52) U.S. Cl. .................... 8/405; 8/406; 8/435; 540/575
(58) Field of Classification Search ...................... 8/405, 8/406, 435; 540/575
See application file for complete search history.

(56) References Cited

U.S. PATENT DOCUMENTS

| 6,165,230 | A | 12/2000 | Rose et al. |
| 6,537,959 | B2 | 3/2003 | Appel et al. |
| 7,211,116 | B2 | 5/2007 | Kiyomine et al. |
| 7,270,683 | B2 | 9/2007 | Abe et al. |
| 2005/0102769 | A1* | 5/2005 | Sabelle et al. .................. 8/405 |

FOREIGN PATENT DOCUMENTS

| JP | 2001 513766 | 9/2001 |
| JP | 2002-255763 | 9/2002 |
| JP | 2005 504046 | 2/2005 |
| WO | WO 01/85717 A1 | 11/2001 |
| WO | WO 03/051322 A1 | 6/2003 |

OTHER PUBLICATIONS

STIC Search Report dated Mar. 5, 2010.*

* cited by examiner

*Primary Examiner*—Eisa B Elhilo
(74) *Attorney, Agent, or Firm*—Oblon, Spivak, McClelland, Maier & Neustadt, L.L.P.

(57) ABSTRACT

A hair dye composition including a first part containing an alkaline agent and a second part containing an oxidizing agent, which are mixed together immediately before use, wherein at least one of the first part and the second part contains a diazacycloheptane represented by the following general formula (1) or a salt thereof, and the pH of the mixture is 7.5 to 12;

wherein Z represents a hydroxy group, a primary amino group, or a C1 to C4 acyloxy group; $R^1$ and $R^2$ represent H or a C1 to C4 alkyl group which may be branched; and $R^3$ represents H, a C1 to C6 alkyl or C1 to C6 alkoxy group which may be branched, or an aralkyl or aryl group, having a total of 12 or less carbon atoms, which may have been substituted by one or more C1 to C4 alkyl or alkoxy groups.

(1)

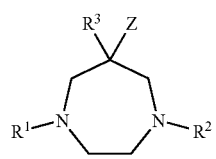

4 Claims, No Drawings

HAIR DYE COMPOSITION

TECHNICAL FIELD

The present invention relates to a hair dye composition including a first part containing an alkaline agent and a second part containing an oxidizing agent, which are mixed together immediately before use.

BACKGROUND OF THE INVENTION

A two-part permanent hair dye composed of the first part containing an alkaline agent and an acid dye intermediate and the second part containing an oxidizing agent has been broadly used for dyeing hair. The two-part permanent hair dye works in general according to a mechanism that the hair is dyed while it is bleached. The oxidizing agent contained in the second part works to generate a dye by an oxidative coupling reaction of the acid dye intermediate, and at the same time to lighten the hair by oxidatively decomposing melanin therein. The alkaline agent contained in the first part works to promote the dyeing action as well as the bleaching action by enhancing the activity of the oxidizing agent. Recently fashion hair coloring, namely enjoying a whole or part of the hair dyed in various colors, has been well accepted by consumers, while sufficient bleaching is required to dye the hair in a brighter color than the original hair color. Further, for coloring gray hair for masking, sufficient bleaching is required to achieve a brighter tone than the original hair color and to achieve a satisfactory masking effect. Since the bleaching activity on the hair depends on the quantity of the alkali and the oxidizing agent, when the hair dye is used for such purposes, large amounts of the alkali and the oxidizing agent are especially required.

Although as an alkaline agent ammonia and an organic amine, and as an oxidizing agent hydrogen peroxide are broadly used, if a large amount thereof is used in order to obtain sufficient bleaching activity, it may raise a problem that the hair is damaged or the scalp is irritated, depending on the amount used.

In some cases, persulfate having strong oxidizing activity is added as the third part in order to dye the hair very bright, in other words, to oxidatively decompose melanin thoroughly, which has, however, drawbacks that severe damage of hair proteins may be caused by the nonselective strong oxidation activity of the persulfate, and that, as another serious problem, the dye produced by the coupling is decomposed by the persulfate leading to a decrease in dyeability contrary to the intention.

Use of certain amines has been proposed to solve the problems (e.g. Patent Documents 1 and 2); however their performance has not been adequate for the bleaching performance required in recent years.

Use of some diazacycloheptanes in a bleaching agent for textiles as a bleaching catalyst has been known (Patent Documents 3 and 4). But the disclosure is limited to the use of diazacycloheptanes with manganese, etc. as metal complexes, and there has been no indication whatsoever about the use thereof in a two-part hair dye for hair.

[Patent Document 1] JP-A-2002-255763
[Patent Document 2] WO2003/051322
[Patent Document 3] WO2001/85717
[Patent Document 4] U.S. Pat. No. 6,537,959

DISCLOSURE OF THE INVENTION

The present invention provides a hair dye composition including a first part containing an alkaline agent and a second part containing an oxidizing agent, which are mixed together immediately before use, wherein at least one of the first part and the second part contains a diazacycloheptane represented by the following general formula (1) or a salt thereof, and the pH after mixing is 7.5 to 12.

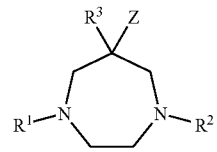

(1)

wherein Z represents a hydroxy group, a primary amino group, or a C1 to C4 acyloxy group which may be branched;

$R^1$ and $R^2$ are the same or different, and each represents a hydrogen atom or a C1 to C4 alkyl group which may be branched; and $R^3$ represents a hydrogen atom, a C1 to C6 acyclic or cyclic alkyl group which may be branched, a C1 to C6 acyclic or cyclic alkoxy group which may be branched, an aralkyl group having a total of 12 or less carbon atoms, which may be substituted by one or more C1 to C4 alkyl or alkoxy groups, or an aryl group having a total of 12 or less carbon atoms, which may be substituted by one or more C1 to C4 alkyl or alkoxy groups.

MODE FOR CARRYING OUT THE INVENTION

The present invention relates to a two-part or three-part hair dye composition, which causes little damage to the hair and irritation to the scalp upon application, and has superior bleaching and dyeing activities on the hair.

The present inventors have discovered that by adding a certain diazacycloheptane to the hair dye composition without forming a metal complex, the hair dye composition having excellent bleaching activity on the hair, capable of dyeing the hair in bright and favorable colors, and reducing damage to the hair and irritation to the scalp can be provided.

In the present invention, a "hair dye" includes a hair dyeing agent containing a dye as well as a hair bleaching agent without containing a dye. Furthermore, "to dye hair" means, in the case of a hair dye containing a dye, to bleach and dye the hair, and in the case of a hair bleaching agent without containing a dye, to bleach the hair. The hair dye of the present invention may be in a form of a two-part type including the first part containing an alkaline agent and the second part containing an oxidizing agent, or a three-part type including additionally the third part of an oxidizing aid containing granulated persulfate, etc. "Total composition" means herein the whole composition mixture of the components constituting the hair dye ready for application.

In diazacycloheptanes represented by the general formula (1) (hereinafter referred to as a "diazacycloheptane (1)") to be used in the present invention, the C1 to C4 acyloxy group which may be branched, represented by Z includes an acetoxy group, an ethylcarbonyloxy group, a propylcarbonyloxy group, and an isopropylcarbonyloxy group;

the C1 to C4 alkyl group which may be branched, represented by $R^1$ and $R^2$ includes a methyl group, an ethyl group, a propyl group, an isopropyl group, an n-butyl group, a sec-butyl group and a tert-butyl group; and the C1 to C6 acyclic or cyclic alkyl group which may be branched, represented by $R^3$ includes a methyl group, an ethyl group, a propyl group, an isopropyl group, an n-butyl group, a sec-butyl group, a tert-butyl group, an n-pentyl group, an n-hexyl group, a 2-ethylbutyl group, a 3-ethylbutyl group, a cyclohexyl group, a cyclopentyl group, a 2-methylcyclopentyl group, a 3-methylcyclopentyl group, a 1-methylcyclopentyl group, and a cyclopentylmethyl group; as the C1 to C6 acyclic or cyclic alkoxy group which may be branched, a methoxy group, an ethoxy group, a propoxy group, an isopropoxy group, an n-butoxy group, a sec-butoxy group, a tert-butoxy group, an n-pentyloxy group, an n-hexyloxy group, a 2-ethylbutoxy group, a 3-methylpentyloxy group, a cyclohexyloxy group, a cyclopentyloxy group, a 2-methylcyclopentyloxy group, a 3-methylcyclopentyloxy group, a 1-methylcyclopentyloxy group, and a cyclopentylmethoxy group; as the aralkyl group having a total of 12 or less carbon atoms, which may be substituted by one or more C1 to C4 alkyl or alkoxy groups, a benzyl group, a phenethyl group, a 4-methoxybenzyl group, a 3-methoxybenzyl group, a 2-methoxybenzyl group, a 4-ethylbenzyl group, a 3-methylbenzyl group, a 2-methylbenzyl group, a 3,5-dimethylbenzyl group, a 2,6-dimethylbenzyl group, a 2-methylphenethyl group, a 3-methoxyphenetyl group, a 4-methoxyphenetyl group, a 5-methoxyphenetyl group, and a (4-methyl-1-naphthyl)methyl group; and as the aryl group, which may be substituted by one or more C1 to C4 alkyl or alkoxy groups, a phenyl group, a 4-methoxyphenyl group, a 3-methoxyphenyl group, a 2-methoxyphenyl group, a 4-isopropoxyphenyl group, a 4-ethylphenyl group, a 3-methylphenyl group, a 2-methylphenyl group, a 3,5-dimethylphenyl group, a 2,6-dimethylphenyl group, a 1-naphthyl group and a 2-naphthyl group.

More preferable examples of the diazacycloheptane (1) are shown below.

Compound 1
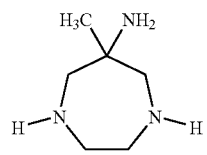

Compound 2
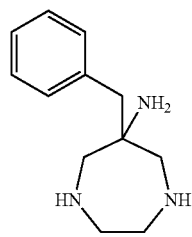

Compound 3
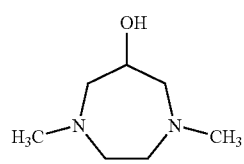

Compound 4
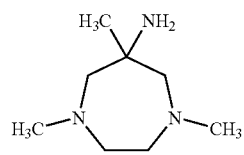

-continued

Compound 5
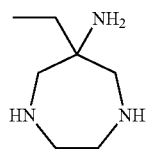

Compound 6
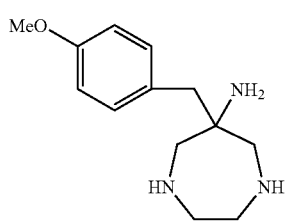

Compound 7
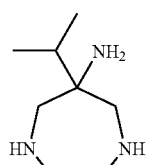

Compound 8
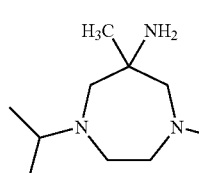

Compound 9
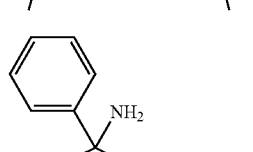

Compound 10
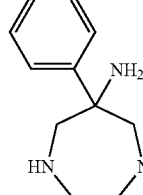

Compound 11
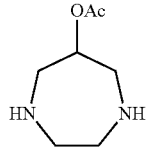

Compound 12
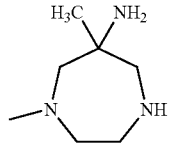

In the case where the diazacycloheptane (1) has an asymmetric carbon atom, either S-isomer or R-isomer, or any mixture thereof may be used. Preferable examples of a salt of the diazacycloheptane (1) include salts of an inorganic or organic acid, such as hydrochloric acid, sulfuric acid, hydrobromic acid, perchloric acid, hydriodic acid, phosphoric acid, acetic acid, propionic acid, lactic acid, citric acid, succinic acid, methanesulfonic acid, and methylsulfuric acid.

One or more of the diazacycloheptanes (1) and the salts thereof may be used, which may be contained in at least one of the first part and the second part, and preferably contained in the first part. The content thereof is preferably 0.01 to 10% by mass, more preferably 0.05 to 3% by mass of the total composition in view of sufficient bleaching and dyeing activities.

Examples of the alkaline agent to be contained in the first part include ammonia, alkanolamines, such as monoethanolamine, isopropanolamine, 2-amino-2-methylpropanol and 2-aminobutanol, alkanediamines such as 1,3-propanediamine, and carbonates, such as ammonium carbonate, ammonium hydrogen carbonate, guanidine carbonate, sodium carbonate, potassium carbonate, sodium hydrogen carbonate and potassium hydrogen carbonate. Among them ammonia and the alkanolamines are preferable, and among the alkanolamines monoethanolamine is more preferable. These alkaline agents may be contained singly or in combination of two or more in the first part. Although the content may be appropriately chosen insofar as the pH falls within a required range, it is preferably 0.05 to 10% by mass, more preferably 0.1 to 5% by mass and even more preferably 0.2 to 3% by mass of the total composition from the standpoints of sufficient bleaching and dyeing activities and reduction in the hair damage and scalp irritation.

Examples of the oxidizing agent to be contained in the second part include hydrogen peroxide and hydrogen peroxide generating agents, such as urea peroxide, melamine peroxide, sodium perborate, potassium perborate, sodium percarbonate and potassium percarbonate, and hydrogen peroxide is preferable owing to its high degree of freedom in formulation. The content of the oxidizing agent reduced to a hydrogen peroxide quantity is 0.1 to 12% by mass, more preferably 0.5 to 9% by mass and even more preferably 1 to 6% by mass of the total composition from the standpoints of sufficient bleaching and dyeing activities and reduction in the hair damage and scalp irritation.

The hair dye composition of the present invention should preferably contain additionally one or more chelating agents publicly known for use in a hair dye composition, such as ethylenediaminetetraacetic acid, ethylenediamine hydroxyethyl triacetate, diethylenetriamine pentaacetic acid and alkaline salts thereof, so that the diazacycloheptanes (1) are prevented from forming a metal complex and the oxidizing agent and the alkaline agent can work in the hair more effectively. The content of the chelating agent is preferably in the range of 0.01 to 5% by mass in view of sufficient bleaching and dyeing activities. The chelating agent may be contained in either or both of the first part and the second part.

In the case where the composition of the present invention is a hair dyeing agent containing a dye, an oxidizing dye intermediate or a direct dye is contained in the first part as the dye. In the case where the composition of the present invention is a hair bleaching agent, the dyes are not contained.

As the oxidizing dye intermediate suitable for the hair dye composition of the present invention, such precursors and couplers can be used, as are publicly known and used ordinarily for hair dyes.

Examples of the precursor include p-phenylenediamine, toluene-2,5-diamine, 2-chloro-p-phenylenediamine, p-aminophenol, p-methylaminophenol, o-aminophenol, 2,4-diaminophenol, N-phenyl-p-phenylenediamine, and salts thereof. The salts are those of the same organic and inorganic acids as in the aforedescribed case of the diazacycloheptanes (1).

Examples of the coupler include m-phenylenediamine, 2,4-diaminophenoxyethanol, m-aminophenol, p-amino-o-cresol, 2-methyl-5-(2-hydroxyethylamino)phenol, resorcin, 1-naphthol, 1,5-dihydroxynaphthalene, hydroquinone, and salts thereof. The salts are those of the same organic and inorganic acids as in the aforedescribed case of the diazacycloheptanes (1).

The precursor and the coupler can be used respectively singly or in combination of two or more, and the preferable contents thereof are respectively 0.01 to 5% by mass, and more preferably 0.1 to 4% by mass of the total composition.

Meanwhile, as for the direct dye, an acid dye, a basic dye, a disperse dye and a reactive dye publicly known for use in a hair dye can be used. Examples of the acid dye include Blue No. 1, Violet No. 401, Black No. 401, Orange No. 205, Red No. 227, Red No. 106, Yellow No. 203, and Acid Orange 3. Examples of the basic dye include Basic Blue 99, Basic Brown 16, Basic Brown 17, Basic Red 76, and Basic Yellow 57. Examples of the direct dyes other than the acid dye and the basic dye include 2-nitro-p-phenylenediamine, 2-amino-6-chloro-4-nitrophenol, 3-nitro-p-hydroxyethylaminophenol, 4-nitro-o-phenylenediamine, 4-amino-3-nitrophenol, 4-hydroxypropylamino-3-nitrophenol, N,N-bis(2-hydroxyethyl)-2-nitro-p-phenylenediamine, Disperse Violet 1, Disperse Blue 1, Disperse Black 9, HC Blue No. 2, HC Orange No. 1, HC Red No. 1, HC Red No. 3, HC Yellow No. 2, HC Yellow No. 4, and HC Yellow No. 5.

The direct dyes can be used singly or in combination of two or more, and the preferable content thereof is 0.001 to 5% by mass, and more preferably 0.01 to 4% by mass of the total composition. Furthermore, the oxidizing dye intermediate and the direct dye can be used together, and thereby the total amount of the oxidizing dye intermediate and the direct dye is preferably 0.05 to 10% by mass, and more preferably 0.1 to 8% by mass of the total composition.

The hair dye composition of the present invention may further include a conditioning component suitable for application to the hair. Examples of a suitable conditioning component to be incorporated into the hair dye composition of the present invention include silicones, such as a silicone oil, a cationic silicone, a silicone gum and a silicone resin, organic conditioning oils, such as a hydrocarbon oil, a polyolefin, an aliphatic ester and an aliphatic amide, and a conditioning polymer. The content of the conditioning component is preferably 0.01 to 20% by mass, more preferably 0.05 to 15% by mass, and even more preferably 0.5 to 5% by mass of the total composition.

Examples of the silicones include the following.

(Silicones-1) Dimethicone, Dimethiconol, and Cyclomethicone

Silicones-1 includes those represented by the following general formula (2).

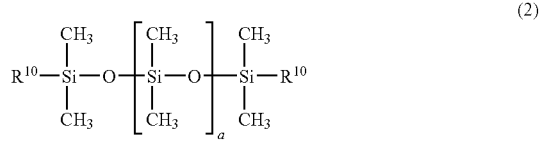

wherein $R^{10}$ represents a methyl group or a hydroxy group, or the two $R^{10}$ may be a single oxygen atom forming a ring, and "a" represents a number of 1 to 20,000.

Silicones-1 also include BY11-026, BY22-19, and FZ-3125 from Dow Corning Toray Co., Ltd. Further, a highly-polymerized dimethylpolysiloxane dissolved or dispersed in a liquid oil (e.g. a liquid silicone oil such as a low-polymerized dimethylpolysiloxane and cyclomethicone, and a liquid hydrocarbon oil such as isoparaffin) may be used.

(Silicones-2) Amino-Modified Silicone

Although various amino-modified silicones may be used, compounds known as amodimethicone according to the INCI nomenclature represented by the following general formula (3) with an average molecular weight of about 3,000 to 100,000 are preferable.

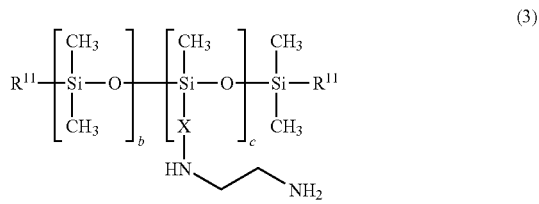

wherein $R^{11}$ represents a methyl group or a hydroxy group, X represents a C2 to C6 divalent hydrocarbon group, and "b" and "c" represent a number of 1 to 20,000.

The amino-modified silicone is preferably used as an aqueous emulsion, and includes SM8704C (Dow Corning Toray Co., Ltd.) and DC929 (Dow Corning Corp.) commercially available.

Other amino-modified silicones include bis(C13 to C15 alkoxy) PG-amodimethicone represented by the following formula (4), and 8500 Conditioning Agent (Dow Corning Corp.) commercially available.

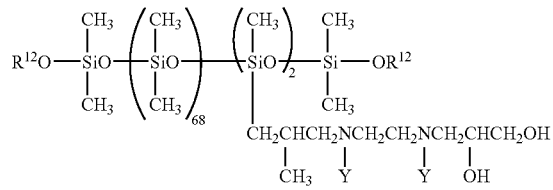

wherein $R^{12}$ represents a C13 to C15 linear or branched alkyl group and 75% of Y represents a group of —CH$_2$CH(OH)CH$_2$OH and 25% represents a hydrogen atom.

Furthermore, a block copolymer of the amino-modified silicone with a polyoxyalkylene is also preferable, and is, for example, bis-isobutyl PEG-15/amodimethicone as represented by the following general formula (5).

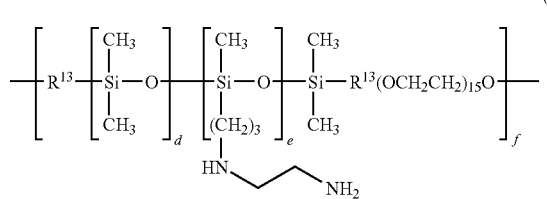

wherein $R^{13}$ represents an isobutylene group, "d" represents a number of 2 or higher, preferably a number of 2 to 1,000, "e" represents a number of 1 or higher, preferably a number of 1 to 50, and "f" represents a number of 2 or higher, preferably a number of 2 to 100.

For example, commercially available FZ-3798 and silicone SS-3588 both from Dow Corning Toray Co., Ltd. are included.

(Silicones-3) Polyether-Modified Silicone

Although various polyether-modified silicones may be used, compounds derived from dimethicone by substituting a part of the methyl groups with polyethylene glycol, with an average molecular weight of about 3,000 to 100,000, known as PEG-n dimethicone according to the INCI nomenclature (e.g. PEG-3 dimethicone, PEG-7 dimethicone, PEG-8 dimethicone, PEG-9 dimethicone, PEG-10 dimethicone, PEG-12 dimethicone and PEG-14 dimethicone) represented by the following general formula (6), or known as Polysilicone-13 according to the INCI nomenclature represented by the following general formula (7) are preferable.

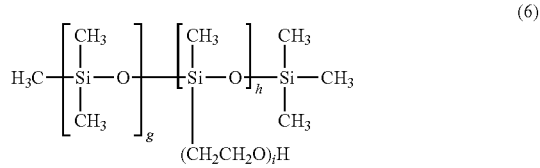

wherein "g" and "h" represent a number of 1 to 1,000, and "i" represents a number of 1 to 2,000.

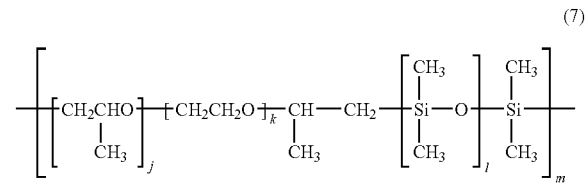

wherein "j", "k" and "l" represent a number of 1 to 1,000, and "m" represents a number of 1 to 2,000.

(Silicones-4) Other Silicones

In addition, the silicones also include methylphenylpolysiloxane, a fatty acid-modified silicone, an alcohol-modified silicone, an alkoxy-modified silicone, an epoxy-modified silicone, a fluorine-modified silicone and an alkyl-modified silicone.

The silicones diluted or dispersed in a volatile silicone or a nonvolatile silicone, or existing as dispersed liquid droplets in an aqueous surfactant may be also used.

The organic conditioning oil is preferably a low viscosity, water insoluble liquid, and includes a hydrocarbon oil, a polyolefin, an aliphatic ester, a fatty acid amide, and a mixture thereof. The viscosity of the organic conditioning oil measured at 40° C. is preferably 1 to 200 mPa·s, more preferably 1 to 100 mPa·s, and even more preferably 2 to 50 mPa·s.

Examples of the aliphatic ester include an ester with a hydrocarbon chain derived from a fatty acid and an alcohol (e.g. a monoester, a polyhydric alcohol ester, and a di- or tri-carboxylic acid ester). The hydrocarbon group of the aliphatic ester may have another compatible functional moiety, such as an amide group, an alkoxy group, and a polyoxyalkylene group, or the hydrocarbon group may be covalently bonded thereto. Specific examples of a preferable aliphatic ester include isopropyl myristate and octyldodecyl myristate.

Examples of the aliphatic amide include an amide with a hydrocarbon chain derived from a fatty acid and an alkylamine or an alkanolamine. The hydrocarbon group of the aliphatic amide may have another compatible functional moiety, such as an amide group, an alkoxy group, and a polyoxyalkylene group, or the hydrocarbon group may be covalently bonded thereto. Specific examples of a preferable aliphatic amide include oleic acid diethanolamide, lauric acid diethanolamide, coconut oil fatty acid amide, and coconut oil fatty acid diethanolamide.

As the conditioning polymer a cationic polymer is preferable but additionally an anionic, a nonionic and/or an amphoteric polymer may be contained, provided that the total amount of the polymers should be within the aforedescribed range irrespective of the types of the polymers.

Any anionic counter ion of the cationic polymer may be used, insofar as the cationic polymer is in a dissolved state in the composition, and the counter ion is physically and chemically compatible with the essential components of the hair dye composition, or should not impair substantially the performance, stability or appearance of the product. Examples of the counter ion include, but not limited to, a halide ion (e.g. a chloride ion, a fluoride ion, a bromide ion and an iodide ion), a sulfate ion, a methylsulfate ion and a mixture thereof.

Examples of the cationic polymer to be favorably used for the hair dye composition of the present invention include, but is not limited to, a cationic polysaccharide (e.g. a cationic cellulose derivative, and cationic guar), a copolymer of a vinyl monomer having a protonated amine substituent or a quaternary ammonium substituent, with a water-soluble monomer, a vinyl pyrrolidone copolymer and a cationic protein.

The hair dye composition of the present invention may contain additionally a selected polyalkylene glycol suitable for application to the hair, and the content thereof is 0.005 to 1.5% by mass of the total composition, preferably 0.025 to 1.2% by mass, more preferably 0.05 to 1% by mass, and even more preferably 0.1 to 0.5% by mass. The polyalkylene glycol is required to be physically and chemically compatible with other formulated components, and not to impair substantially the stability, appearance or performance of the product. Specific examples thereof include polyethylene glycol, polypropylene glycol, and a mixture thereof or a copolymer of ethylene oxide and propylene oxide may be also used.

For the hair dye composition of the present invention, water and/or an organic solvent is used as a medium. Examples of the organic solvent include a lower alkanol, such as ethanol and 2-propanol, an aromatic alcohol, such as benzyl alcohol and benzyl oxyethanol, a polyol, such as propylene glycol, 1,3-butanediol, diethylene glycol, and glycerin, a cellosolve, such as ethyl cellosolve, butyl cellosolve and benzyl cellosolve, and a carbitol, such as ethyl carbitol, and butyl carbitol.

The hair dye composition of the present invention may include in addition to the above components other components that are ordinarily used as cosmetic raw materials.

Examples of such optional components include a hydrocarbon, an animal/plant fat and oil, a higher fatty acid, a penetration enhancer, a cationic surfactant, a natural or synthetic polymer, a higher alcohol, an ether, an amphoteric surfactant, a nonionic surfactant, a protein derivative, an amino acid, an antiseptic agent, a chelating agent, a stabilizer, an antioxidant, a plant extract, a galenical extract, vitamins, a colorant, a flavor and a UV absorber.

The hair dye composition of the present invention is provided, similarly as a broadly used conventional oxidative hair bleaching or dyeing agent, in a form of a two-part type including the first part containing an alkaline agent and the second part containing an oxidizing agent, or a three-part type including additionally the third part of an oxidizing aid containing granulated persulfate, etc. The formulations of the first part and the second part may be in a form of a liquid, milky liquid, cream, gel, paste and foam, as well as an aerosol. The formulations of the third part of the oxidizing aid may be in a granular form. Examples of the persulfate to be contained include ammonium persulfate, potassium persulfate, and sodium persulfate.

The mixing ratio (by mass) of the first part and the second part in the hair dye composition of the present invention is preferably in the range of 1:0.5 to 1:3 in view of the practical usefulness.

The pH (25° C.) of the hair dye composition of the present invention is preferably for the first part 8 to 12, for the second part 2 to 5, and the pH of the mixture of the first part and the second part is 7.5 to 12, and preferably 8 to 11 in view of the bleaching and dyeing activities and skin irritation. Examples of a pH adjuster include an inorganic acid, such as hydrochloric acid and phosphoric acid, an organic acid, such as citric acid, glycolic acid and lactic acid, a hydrochloride salt, such as ammonium chloride and monoethanolamine hydrochloride, and a phosphate, such as potassium dihydrogen phosphate and disodium hydrogen phosphate.

The viscosity of the hair dye composition of the present invention is preferably so selected that the mixture of the first and second parts upon application to the hair hardly drips. Specifically, the viscosity measured at 25° C. with a B-type rotating viscometer (with rotor No. 3, at 12 rpm, measured after rotation for 1 min) is preferably 2,000 to 100,000 mPa·s.

To dye the hair with the hair dye composition of the present invention, for example, the first part and the second part in the hair dye composition of the present invention are mixed and applied to the hair, left acting at 15 to 45° C. for 1 to 60 min, preferably 5 to 30 min, and then the hair should be washed and dried.

EXAMPLES

Test Example

Evaluation of Melanin Decomposition

<Isolation of Melanin>

Melanin granule was isolated from a black hair not chemically treated previously of an Asian using papain according to a literature-based method (J. Soc. Cosmet. Chem., 1986, vol. 37, p. 159, and J. Soc. Cosmet. Chem., 1995, vol. 46, p. 181). Specifically, to 100 g of the hair cut to 1 cm long were added 3 L of water, 8.3 g of papain and 30 g of dithioerythritol. The mixture was stirred at 50° C. for 72 hours, filtrated and dried to isolate melanin granules.

<Decomposition Test of Melanin>

Each first part shown in Table 1 and Table 2 and the second part shown in Table 3 for oxidative hair bleaching were prepared. To 5 mg of the melanin granule isolated by papain, respectively 1 mL of the first part and the second part were added, and the liquid mixture was stirred at 30° C. for 10 min. to bleach the melanin granule. The pH of the liquid mixture was 10.1 with the first part according to Table 1 and 10.7 with the first part according to Table 2. Phosphoric acid was added to the liquid mixture to adjust its pH to 2 or below, which was then filtered to obtain the residual melanin. The residual melanin was dissolved in 50 mL of a 10% by mass solution of tetramethylammonium hydroxide, and the absorbance of the solution at 600 nm was measured to determine the melanin residual amount for comparison according to a literature-based method (Journal of Society of Cosmetic Chemists of Japan, 1978, vol. 12 (1), p. 39).

TABLE 1

| First part | Test Ex. | | Comp. Test Ex. | | | |
|---|---|---|---|---|---|---|
| (% by mass) | 1 | 2 | 1 | 2 | 3 | 4 |
| Monoethanol amine | 0.55 | 0.55 | 0.55 | 0.55 | 0.55 | 0.55 |
| Compound 1 | 0.3 | — | — | — | — | — |
| Compound 2 | — | 0.50 | — | — | — | — |
| Compound X*1 | — | — | — | 0.3 | — | — |
| Compound Y*2 | — | — | — | — | 0.6 | — |
| Compound Z*3 | — | — | — | — | — | 0.4 |
| Water | balance | balance | balance | balance | balance | balance |

*1

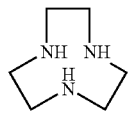

Compound X
(Compound according to Patent Document 1)

*2

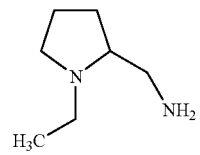

Compound Y
(Compound according to Patent Document 2)

*3

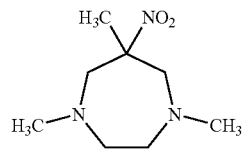

Compound Z
(Compound according to Patent Document 3)

TABLE 2

| First part | Test Ex. | | | Comp. Test Ex. | |
|---|---|---|---|---|---|
| (% by mass) | 3 | 4 | 5 | 5 | 6 |
| Ammonia | 1.7 | 1.7 | 1.7 | 1.7 | 1.7 |
| Ammonium chloride | 0.2 | 0.2 | 0.2 | 0.2 | 0.2 |
| Compound 1 | 0.3 | — | — | — | — |
| Compound 3 | — | 0.5 | — | — | — |
| Compound 4 | — | — | 0.4 | — | — |
| Compound Z*3 | — | — | — | — | 0.4 |
| Water | balance | balance | balance | balance | balance |

TABLE 3

| Common second part | |
|---|---|
| Hydrogen peroxide | 1.40% by mass |
| Water | balance |

The decomposition rate of the melanin granule was calculated from the absorbance of the solution of the untreated melanin granule and the absorbance after the bleaching treatment according to the following formula. The results are shown in Tables 4 and 5.

$$D = (A_1 - A_2)/A_1$$

D: Melanin decomposition rate (%)

$A_1$: Absorbance at 600 nm of the solution of the untreated melanin $A_2$: Absorbance at 600 nm of the solution of the melanin after the bleaching treatment

TABLE 4

| | Test Ex. | | Comp. Test Ex. | | | |
|---|---|---|---|---|---|---|
| | 1 | 2 | 1 | 2 | 3 | 4 |
| D (%) | 43 | 47 | 26 | 39 | 36 | 26 |

TABLE 5

| | Test Ex. | | | Comp. Test Ex. | |
|---|---|---|---|---|---|
| | 3 | 4 | 5 | 5 | 6 |
| D (%) | 58 | 49 | 58 | 31 | 29 |

As obvious from Tables 4 and 5, in Test Examples 1 to 5, although the same amounts of alkali and hydrogen peroxide were used as those of Comparative Examples, the melanin originated from the hair could be decomposed at higher decomposition rates and therefore the bleaching activities were superior to the Comparative Examples.

Example 1 and Comparative Example 1

Evaluation of Dyeability

Each first part shown in Table 6 and the second part shown in Table 7 were prepared to evaluate the dyeability.

TABLE 6

| First part (% by mass) | Ex. 1 | Comp. Ex. 1 |
|---|---|---|
| Compound 1 | 1.0 | — |
| Compound W*4 | — | 1.0 |
| p-Aminophenol | 0.6 | 0.6 |
| m-Aminophenol | 0.45 | 0.45 |
| Toluene-2,5-diamine | 0.17 | 0.17 |
| p-Amino-o-cresol | 0.2 | 0.2 |
| Ammonia (28% by mass) | 8.0 | 8.0 |
| Propylene glycol | 4.0 | 4.0 |
| Stearyltrimonium chloride | 5.0 | 5.0 |
| Ceteth-40 | 2.5 | 2.5 |
| Stearyl alcohol | 8.0 | 8.0 |
| Sodium sulfite | 0.5 | 0.5 |
| Sodium ascorbate | 0.5 | 0.5 |
| Ammonium bicarbonate*5 | q.s. | q.s. |
| Polyquaternium-22 | 5.0 | 5.0 |
| EDTA-4Na | 0.1 | 0.1 |
| Purified water | balance | balance |

*4

TABLE 6-continued

| First part (% by mass) | Ex. 1 | Comp. Ex. 1 |
|---|---|---|

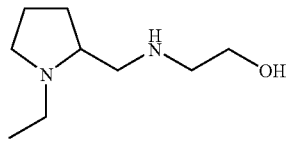

Comparative compound W
(compound according to
Patent Document 2)

*5 Amount to adjust pH to 10

TABLE 7

| Second part | |
|---|---|
| Hydrogen peroxide | 6.0% by mass |
| Purified water | balance |

The first part shown in Table 6 and the second part shown in Table 7 were mixed at the mixing ratio (by mass) of 1:1.5 (pH after mixing was 9.7), and the mixture was applied to a gray hair tress at the bath ratio (dye:hair) of 1:1. The tress was left acting at 30° C. for 20 min., then rinsed with water at 40° C., washed with a commercial shampoo, rinsed with water, treated with a commercial conditioner, rinsed with water and then dried with a towel.

The color of the tress dyed according to the above dyeing treatment was measured by a calorimeter (Colorimeter CR-400 from Konica Minolta Sensing, Inc.) according to the CIE calorimetric system ($L^*$, $a^*$, $b^*$), and $\Delta E^*$ was calculated according to the following formula. The higher $\Delta E^*$ indicates superior dyeability. The results are shown in Table 8.

$$\Delta E^* = \sqrt{(L^*_2 - L^*_1)^2 + (a^*_2 - a^*_1)^2 + (b^*_2 - b^*_1)^2} \quad \text{[Equation 1]}$$

wherein $L^*_1$, $a^*_1$, $b^*_1$ are the measured values before dyeing, and $L^*_2$, $a^*_2$, $b^*_2$ are the measured values after dyeing.

TABLE 8

| | Ex. 1 | Comp. Ex. 1 |
|---|---|---|
| $L^*$ | 39.6 | 46.8 |
| $a^*$ | 12.3 | 10.9 |
| $b^*$ | 14.5 | 15.9 |
| $\Delta E^*$ | 36.2 | 30.3 |

As obvious from the $\Delta E^*$ values shown in Table 8, Example 1 is superior in dyeability to Comparative Example 1, both of which have the same composition except that the nitrogen-containing compounds (Compound 1 or Compound W) are different.

Example 2 and Comparative Example 2

Evaluation of Feel

Each first part shown in Table 9 and the second part shown in Table 7 were mixed at the ratio (by mass) of 1:1.5 (pH after mixing was 9.8), and the mixture was applied to a tress of black hair not chemically treated previously in the same amount. The tress was left acting at 30° C. for 30 min, then rinsed with water at 40° C., washed with a commercial shampoo, rinsed with water and then dried.

TABLE 9

| First part (% by mass) | Ex. 2 | Comp. Ex. 2 |
|---|---|---|
| Compound 2 | 0.6 | — |
| Cetyl alcohol | 10 | 10 |
| Sodium lauryl sulfate | 3.0 | 3.0 |
| Oleyl alcohol | 2.0 | 2.0 |
| Ammonia | 0.84 | 0.84 |
| Ammonium chloride*6 | 0.2 | 0.2 |
| EDTA-4Na | 0.1 | 0.1 |
| Purified water | balance | balance |

*6 Amount to adjust pH to 10

The treated bleached hair tress was combed with fingers and the friction feel on fingers was scored according to the following criteria, and the average scores of 4 evaluators are shown in Table 10. The higher score means lower friction.
2: Substantially no friction feel,
1: Slight friction feel, and
0: Obvious friction feel.

TABLE 10

| | Ex. 2 | Comp. Ex. 2 |
|---|---|---|
| Feel rating score | 1.8 ± 0.6 | 0.5 ± 0.6 |

As obvious from Table 10, Example 2 is superior by showing better finger combability to Comparative Example 2, which has the same composition except that the diazacycloheptane is not contained.

Formulation Examples 1 to 3

Formulation Examples 1 to 3 of the two-part hair dye composition are shown in Table 11. The pH of each 1:1 mixture (by mass) of the first parts and the second parts according to Table 11 is 9.8.

TABLE 11

| | | Formulation Ex. | | |
|---|---|---|---|---|
| | Components (% by mass) | 1 | 2 | 3 |
| First part | Compound 1 | 0.75 | 0.5 | — |
| | Compound 2 | — | 0.5 | — |
| | Compound 3 | — | — | 1.5 |
| | p-Aminophenol | 0.10 | — | 0.1 |
| | 2-Hydroxyethyl-p-phenylenediamine sulfate | — | 0.2 | — |
| | Toluene-2,5-diamine sulfate | — | 0.3 | — |
| | 5-Amino-o-cresol | 0.10 | — | — |
| | m-Aminophenol | — | 0.3 | 0.1 |
| | HC Blue No. 2 | 050 | — | — |
| | Basic Yellow 57 | — | 01 | 01 |
| | Stearyl alcohol | 8.0 | 8.0 | 8.0 |
| | Cocamide DEA | 4.5 | 4.5 | 4.5 |
| | Glyceryl stearate (SE) | 1.3 | 1.3 | 1.3 |
| | Ceteareth-30 | 4.0 | 4.0 | 4.0 |
| | Sodium lauryl sulfate | 1.0 | 1.0 | 1.0 |
| | Oleic acid | 2.0 | 2.0 | 2.0 |
| | Propylene glycol | 1.5 | 1.5 | 1.5 |
| | PEG-9 dimethicone*7 | — | 1.5 | 1.5 |
| | Hydrolyzed keratin | 0.5 | 0.5 | 0.5 |
| | Panthenol | 0.8 | 0.8 | 0.8 |
| | Ammonia (28% by mass) | 3.0 | 1.0 | — |
| | Ethanolamine | 3.0 | 4.0 | 5.0 |
| | EDTA-4Na | 0.5 | 0.5 | 0.5 |
| | Ammonium chloride*8 | q.s. | q.s. | q.s. |
| | Purified water | balance | balance | balance |
| Second | Hydrogen peroxide | 6.0 | 6.0 | 6.0 |

TABLE 11-continued

| | Components (% by mass) | Formulation Ex. 1 | Formulation Ex. 2 | Formulation Ex. 3 |
|---|---|---|---|---|
| part | Methylparaben | 0.5 | 0.5 | 0.5 |
| | Phosphoric acid*9 | q.s. | q.s. | q.s. |
| | Purified water | balance | balance | balance |

*7KF-6005, Shin-Etsu Chemical Co., Ltd.
*8Amount to adjust pH to 10
*9Amount to adjust pH to 3.5

Formulation Example 4

Formulation Example 4 of the three-part hair dye composition is shown in Table 12. The pH of the 1:1:0.3 mixture (by mass) of the first part, the second part and the third part according to Table 12 is 9.8.

TABLE 12

| | Components (% by mass) | Formulation Ex. 4 |
|---|---|---|
| First part | Compound 1 | 0.5 |
| | p-Aminophenol | 0.6 |
| | Toluene-2,5-diamine | 0.5 |
| | m-Aminophenol | 0.18 |
| | Resorcin | 0.7 |
| | 5-Amino-o-cresol | 0.1 |
| | Propylene glycol | 4.0 |
| | Ascorbic acid | 0.4 |
| | Sodium sulfite | 0.4 |
| | EDTA-4Na | 0.1 |
| | Sodium lauryl sulfate | 1.0 |
| | Ceteth-40 | 2.5 |
| | Cetearyl alcohol | 8.0 |
| | Polyquaternium-22 | 2.5 |
| | Dimethicone*10 | 2.0 |
| | Amodimethicone*11 | 1.0 |
| | Ethanolamine | 1.5 |
| | Ammonia water (28% by mass) | 6.5 |
| | Perfume | 0.5 |
| | Ammonium hydrogencarbonate*12 | q.s. |
| | Purified water | balance |
| Second part | Hydrogen peroxide | 6.0 |
| | Methylparaben | 0.5 |
| | Phosphoric acid*13 | q.s. |
| | Purified water | balance |
| Third part | Sodium persulfate | 10.0 |
| | Potassium persulfate | 16.0 |
| | Ammonium persulfate | 26.0 |
| | Sodium metasilicate | 20.0 |
| | Sodium silicate | 17.8 |
| | Silica | 1.0 |
| | Sodium stearate | 5.0 |
| | Sodium lauryl sulfate | 1.0 |
| | EDTA-4Na | 1.0 |
| | Cyclodextrin | 0.2 |

TABLE 12-continued

| Components (% by mass) | Formulation Ex. 4 |
|---|---|
| Xanthan gum | 1.0 |
| Cellulose gum | 1.0 |

*10BY11-026, Dow Corning Toray Co., Ltd.
*11SM8704C, Dow Corning Toray Co., Ltd.
*12Amount to adjust pH to 10
*13Amount to adjust pH to 3.5

The invention claimed is:

1. A hair dye composition, comprising a first part comprising an alkaline agent and a second part comprising an oxidizing agent, which are mixed together immediately before use, wherein at least one of the first part and the second part comprises a diazacycloheptane represented by the following general formula (1) or a salt thereof, and the pH after mixing is 7.5 to 12;

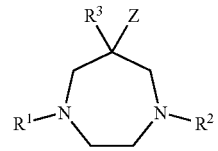
(1)

wherein Z represents a hydroxy group, a primary amino group, or a C1 to C4 acyloxy group which may be branched;
$R^1$ and $R^2$ are the same or different, and each represents a hydrogen atom or a C1 to C4 alkyl group which may be branched; and
$R^3$ represents a hydrogen atom, a C1 to C6 acyclic or cyclic alkyl group which may be branched, a C1 to C6 acyclic or cyclic alkoxy group which may be branched, an aralkyl group having a total of 12 or less carbon atoms, which may be substituted with one or more C1 to C4 alkyl or alkoxy groups, or an aryl group having a total of 12 or less carbon atoms, which may be substituted with one or more C1 to C4 alkyl or alkoxy groups.

2. The hair dye composition according to claim 1, wherein the first part comprises an acid dye intermediate.

3. The hair dye composition according to claim 1 or 2, wherein the first part comprises a direct dye.

4. A method for dyeing hair, comprising the steps of mixing the first part and the second part of the hair dye composition according to claim 1 immediately before use, applying the mixture to the hair, leaving the mixture on the hair for 1 to 60 min, and then washing the mixture off.

* * * * *